United States Patent
Wang et al.

(10) Patent No.: US 10,047,026 B2
(45) Date of Patent: Aug. 14, 2018

(54) PROCESS FOR REDUCING 1233XF CONCENTRATION IN 244BB

(71) Applicant: HONEYWELL INTERNATIONAL INC, Morris Plains, NJ (US)

(72) Inventors: Haiyou Wang, Amherst, NY (US); Daniel C. Merkel, Orchard Park, NY (US); Hsueh Sung Tung, Getzville, NY (US); Michael Gatter, Elk Grove Village, IL (US)

(73) Assignee: HONEYWELL INTERNATIONAL INC, Morris Plains, NJ (US)

( * ) Notice: Subject to any disclaimer, the term of this patent is extended or adjusted under 35 U.S.C. 154(b) by 0 days.

(21) Appl. No.: 15/038,254

(22) PCT Filed: Apr. 22, 2016

(86) PCT No.: PCT/US2016/028746
§ 371 (c)(1),
(2) Date: May 20, 2016

(87) PCT Pub. No.: WO2016/172413
PCT Pub. Date: Oct. 27, 2016

(65) Prior Publication Data
US 2017/0113987 A1    Apr. 27, 2017

Related U.S. Application Data

(60) Provisional application No. 62/152,323, filed on Apr. 24, 2015.

(51) Int. Cl.
C07C 17/389    (2006.01)
C07C 17/087    (2006.01)
C07C 17/25     (2006.01)

(52) U.S. Cl.
CPC .......... *C07C 17/389* (2013.01); *C07C 17/087* (2013.01); *C07C 17/25* (2013.01)

(58) Field of Classification Search
CPC .................................................. C07C 17/389
See application file for complete search history.

(56) References Cited

U.S. PATENT DOCUMENTS

| | | |
|---|---|---|
| 4,820,318 A | 4/1989 | Chang et al. |
| 4,820,681 A | 4/1989 | Chang et al. |
| 4,902,312 A | 2/1990 | Chang |
| 4,906,796 A | 3/1990 | Yates |
| 5,087,778 A | 2/1992 | Yates |
| 5,233,107 A | 8/1993 | Jansen |
| 5,779,998 A | 7/1998 | Tom |
| 6,585,948 B1 | 7/2003 | Ryoo et al. |
| 7,220,697 B2 | 5/2007 | Pak et al. |
| 7,402,544 B2 | 7/2008 | Pak et al. |
| 7,597,744 B2 | 10/2009 | Thomas et al. |
| 7,718,570 B2 | 5/2010 | Pak et al. |
| 8,017,825 B2 | 9/2011 | Kuznicki et al. |
| 8,058,486 B2 | 11/2011 | Merkel et al. |
| 8,337,595 B2 | 12/2012 | Thomas et al. |
| 8,796,493 B2 | 8/2014 | Merkel et al. |
| 9,296,670 B2 * | 3/2016 | Wang ............... B01J 27/08 |
| 2004/0030204 A1 | 2/2004 | Wilmet et al. |
| 2008/0011159 A1 | 1/2008 | Thomas et al. |
| 2009/0187053 A1 | 7/2009 | Kuznicki et al. |
| 2011/0105809 A1 | 5/2011 | Devic et al. |
| 2012/0065437 A1 | 3/2012 | Merkel et al. |
| 2012/0184785 A1 | 7/2012 | Cottrell et al. |
| 2012/0266750 A1 | 10/2012 | Thomas et al. |
| 2013/0085308 A1 | 4/2013 | Merkel et al. |
| 2014/0303409 A1 * | 10/2014 | Wang ............... C07C 17/25 570/134 |
| 2015/0005536 A1 | 6/2015 | Wang et al. |

FOREIGN PATENT DOCUMENTS

| | | |
|---|---|---|
| WO | 90/08751 A1 | 8/1999 |
| WO | 2012/099776 A1 | 7/2012 |
| WO | 2013/049742 A1 | 4/2013 |
| WO | 2013/119919 A1 | 8/2013 |

OTHER PUBLICATIONS

International Search Report and Written Opinion issued in International Application No. PCT/US2016/028746 dated Aug. 1, 2016.

* cited by examiner

*Primary Examiner* — Medhanit W Bahta
(74) *Attorney, Agent, or Firm* — Scully, Scott, Murphy & Presser

(57) ABSTRACT

The present disclosure provides a method for separating 244bb from 1233xf by using solid adsorbent selected from molecular sieves having an average pore size of 5 Å or greater.

26 Claims, No Drawings

US 10,047,026 B2

PROCESS FOR REDUCING 1233XF CONCENTRATION IN 244BB

RELATED APPLICATIONS

The present application is a '371 national phase application of International Application No. PCT/US2016/028746 filed on Apr. 22, 2016 and claims benefit of priority of U.S. Provisional Application No. 62/152,123, filed on Apr. 24, 2015, the contents of both of which are incorporated by reference.

FIELD OF THE DISCLOSURE

This disclosure relates to novel methods for preparing fluorinated organic compounds, and more particularly to methods of producing fluorinated hydrocarbons. More specifically, this disclosure further provides a method for removing 2-chloro-3,3,3-trifluoropropene (HCFO-1233xf) from 2-chloro-1,1,1,2-tetrafluorpropane (HCFC-244bb) using a molecular sieve having a pore size of 5 Å or greater.

BACKGROUND OF THE DISCLOSURE

Hydrofluorocarbons (HFCs), in particular hydrofluoroalkenes, such as tetrafluoropropenes (including 2,3,3,3-tetrafluoro-1-propene (HFO-1234yf or 1234yf)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and, thus, pose no threat to the ozone layer.

In addition to ozone depleting concerns, global warming is another environmental concern in many of these applications. Thus, there is a need for compositions that meet both low ozone depletion standards as well as having low global warming potentials. Certain fluoroolefins are believed to meet both goals. Thus, there is a need for manufacturing processes that provide halogenated hydrocarbons and fluoroolefins that contain no chlorine that also have a low global warming potential. One tetrafluoropropene having valuable properties is 2,3,3,3-tetrafluoropropene (HFO-1234yf). Thus, there is a need for new manufacturing processes for the production of tetrafluoropropenes and in particular 2,3,3,3-tetrafluoropropene.

HCFC-244bb is an intermediate in the production of 2,3,3,3-tetrafluoropropene (HFO-1234yf) which is well known in the art. U.S. Pat. No. 8,058,486, the contents of which are incorporated by reference, discloses a process of making HFO-1234yf starting with chlorinated hydrocarbons. The process has three-steps as follows:
 (i) $(CQ_2=CCl-CH_2Q$ or $CQ_3-CCl=CH_2$ or $CQ_3-CHCl-CH_2Q)+HF\rightarrow$ 2-chloro-3,3,3-trifluoropropene (HCFO-1233xf or 1233xf)+HCl in a vapor phase reactor charged with a solid catalyst;
 (ii) 2-chloro-3,3,3-trifluoropropene (HCFO-1233xf)+ HF→2-chloro-1,1,1,2-tetrafluoropropane (HCFC-244bb or 244bb) in a liquid phase reactor charged with a liquid hydrofluorination catalyst; and
 (iii) 2-chloro-1,1,1,2-tetrafluoropropane (HCFC-244bb) →2,3,3,3-tetrafluoropropene (HFO-1234yf) in a vapor phase reactor.

wherein Q is independently selected from F, Cl, Br, and I, provided that at least one Q is not fluorine.

The first step involves fluorination of tetrachloropropene or pentachloropropane with HF to produce HCFO-1233xf. The second step involves hydrofluorination of HCFO-1233xf with HF to produce HCFC-244bb. However, the conversion of HCFO-1233xf is not complete. Some of unreacted HCFO-1233xf is recycled back into the second step hydrofluorination reactor, but some of HCFO-1233xf is carried forward into the third step dehydro-chlorination reactor. The third and final step involves dehydrochlorination of HCFC-244bb to produce HFO-1234yf product. Again, conversion of HCFC-244bb is not complete. Unreacted HCFC-244bb and HCFO-1233xf carried from the third step reactor are recycled back to the second step reactor. But, the presence of HCFO-1233xf in the third step reactor feed does not allow recycle of all unreacted HCFC-244bb to the third step reactor. This results in larger size (lower capacity) of the second step reactor. Also, recycle of HCFC-244bb back into the second step hydrofluorination reactor may result in the formation of over fluorinated by-products such as 1,1,1,2,2-pentafluoropropane (HFC-245cb) and increased HF consumption.

It would be preferred to remove HCFO-1233xf and other halogenated olefins impurities produced in the first two process steps from the HCFC-244bb intermediate product prior to sending the feed into the dehydrochlorination reactor to produce final product HFO-1234yf. This would allow recycle of all unreacted HCFC-244bb back to the third step reactor minimizing the yield loss.

Unfortunately, HCFC-244bb and HCFO-1233xf are inseparable using conventional separation techniques known in the art since HCFC-244bb and HCFO-1233xf form a binary azeotrope or azeotrope-like composition which is described in U.S. Pat. No. 7,803,283. Since the boiling points of 1233xf and 244bb are only about 2° C. apart, separation of them is difficult and expensive.

Moreover, the presence of 2-chloro-3,3,3-trifluoropropene (HCFO-1233xf) in the reaction starting materials, such as HCFC-244bb feedstock, can lead to dramatically reduced conversion of HCFC-244bb to HFO-1234yf as well as increased formation of undesired trifluoropropyne ($CF_3CCH$) byproduct through its dehydrochlorination. In addition, the 2-chloro-3,3,3-trifluoropropene copresence in the starting material, when subjected to dehydrochlorination, can lead to the formation of oligomers, which can produce tar. This result is disadvantageous from the standpoint of a reduced yield of the desired product.

One technique to remove 1233xf from 244bb is described in US 2013/0085308, the contents of which are incorporated herein by reference, which employs activated carbon as an adsorbent. US2013/0085308 additionally reports, at Example 4, that a molecular sieve of 4 Å pore size was unsuccessful in separating 1233xf and 244bb. Regenerating the activated carbon is economically important. US 2013/0085308 discloses that the activated carbon used to separate 1233xf from 244bb can be regenerated by heating, vacuum or an inert gas stream. Nevertheless, there is a need for other techniques to separate 1233xf and 244bb, and a need for other adsorbents and other methods of regenerating these.

The present invention fulfills that need.

SUMMARY OF THE DISCLOSURE

The present specification provides a method to separate 2-chloro-3,3,3,-trifluoropropene (HCFO-1233xf) from 2-chloro-1,1,1,2-tetrafluoropropane (HCFC-244bb) using a solid adsorbent selected from molecular sieves having an average pore size of 5 Å or greater.

DETAILED DESCRIPTION OF THE DISCLOSURE

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

The present disclosure using molecular sieves for separating 2-chloro-3,3,3,-trifluoropropene (HCFO-1233xf) from 2-chloro-1,1,1,2-tetrafluoropropane (HCFC-244bb). The separation is realized by preferential adsorption of HCFO-1233xf over the aforementioned molecular sieves resulting in a higher purity of HCFC-244bb. As defined, molecular sieves include silicalite and carbon molecule sieves and zeolites.

Silicalite is a substantially aluminum-free molecular sieve that is described in U.S. Pat. Nos. 4,061,724 and 4,104,294. The crystalline organosilicates of silicalite are substantially free of alumina. More specifically, the molar ratio of alumina to silica will be in the range of zero to less than 0.002. The pore diameter of the Silicalite is about 5.5 Angstroms. As an adsorbent, it is thus capable of being used for size-selective separations of mixtures of hydrocarbon molecules, and due to its organophilic character is suitable for the selective adsorption of organic molecules from highly polar media such as water.

Zeolites can be generically described as complex aluminosilicates characterized by three-dimensional framework structures enclosing cavities occupied by ions and water molecules, all of which can move with significant freedom within the zeolite matrix. In commercially useful zeolites, the water molecules can be removed from or replaced within the framework structures without destroying the zeolite's geometry. Zeolites usually contain, in addition, metal cations of various metals, including sodium, calcium, potassium, magnesium and barium. In an embodiment, the zeolite can be generally represented by the following formula: $M_{2/n}OAl_2O_3xSiO_2yH_2O$; wherein M is a cation of valence n (e.g., n is 1 or 2), x is greater than or equal to 2y and is a number determined by the porosity and the hydration state of the zeolite, generally from 0 to 8, and y is a number from 0 to 4. In naturally occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

Carbon molecular sieves have been found to be useful in the present invention. Carbon molecular sieves are derived from natural materials such as coal or from man-made polymers such as discussed in U.S. Pat. Nos. 4,820,681 and 6,670,304 and US Publication No. 2002/0025290. These carbon molecular sieves are clearly distinguished from activated carbons, which are also derived from natural materials but have much larger pore sizes. The carbon molecular sieves useful for the separation described herein have an average pore size of 5.0 Angstroms or greater.

Molecular sieves that are serviceable include without limitation zeolites such as 13X, ZSM-5, H-ZSM-5, MFI or silicalite (an Al-free version of ZMS-5), and combinations thereof. In an embodiment, the average pore size is about 5.5 Å or greater. In an embodiment the average pore size ranges from 5.0 to about 20 Å and in another embodiment from about 5.5 Å to about 20 Å. Other preferred average pore sizes include 5.0 Å, 5.5 Å, 6 Å, 6.5 Å, 7 Å, 7.5 Å, 8 Å, 8.5 Å, 9 Å, 9.5 Å, 10 Å, 10.5 Å, 11.0 Å, 11.5 Å, 12.0 Å, 12.5 Å, 13.0 Å, 13.5 Å, 14.0 Å, 14.5 Å, 15.0 Å, 15.5 Å, 16.0 Å, 16.5 Å, 17.0 Å, 17.5 Å, 18.0 Å, 18.5 Å, 19.0 Å, 19.5, and 20.0 Å and all ranges in between 5.0 Å and 20.0 Å. An embodiment of the present invention uses a molecular sieve having an average pore size greater than 5.0 Å, such as 5.1 Å, 5.2 Å, 5.3 Å, 5.4 Å, 5.5 Å, 5.6 Å, 5.7 Å, 5.8 Å, 5.9 Å, 6.0 Å, 6.1 Å, 6.2 Å, 6.3 Å, 6.4 Å, 6.5 Å, 6.6 Å, 6.7 Å, 6.8 Å, 6.9 Å, 7.0 Å, 7.1 Å, 7.2 Å, 7.3 Å, 7.4 Å, 7.5 Å, 7.6 Å, 7.7 Å, 7.8 Å, 7.9 Å, 8.0 Å, 8.1 Å, 8.2 Å, 8.3 Å, 8.4 Å, 8.5 Å, 8.6 Å, 8.7 Å, 8.8 Å, 8.9 Å, 9.0 Å, 9.1 Å, 9.2 Å, 9.3 Å, 9.4 Å, 9.5 Å, 9.6 Å, 9.7 Å, 9.8 Å, 9.9 Å, 10.0 Å, 10.1 Å, 10.2 Å, 10.3 Å, 10.4 Å, 10.5 Å, 10.6 Å, 10.7 Å, 10.8 Å, 10.9 Å. 11.0 Å, 11.1 Å, 11.2 Å, 11.3 Å, 11.4 Å, 11.5 Å, 11.6 Å, 11.7 Å, 11.8 Å, 11.9 Å, 12.0 Å, 12.1 Å, 12.2 Å, 12.3 Å, 12.4 Å, 12.5 Å, 12.6 Å, 12.7 Å, 12.8 Å, 12.9 Å, 13.0 Å, 13.1 Å, 13.2 Å, 13.3 Å, 13.4 Å, 13.5 Å, 13.6 Å, 13.7 Å, 13.8 Å, 13.9 Å, 14.0 Å, 14.1 Å, 14.2 Å, 14.3 Å, 14.4 Å, 14.5 Å, 14.6 Å, 14.7 Å, 14.8 Å, 14.9 Å, 15.0 Å, 15.1 Å, 15.2 Å, 15.3 Å, 15.4 Å, 15.5 Å, 15.6 Å, 15.7 Å, 15.8 Å, 15.9 Å, 16.0 Å, 16.1 Å, 16.2 Å, 16.3 Å, 16.4 Å, 16.5 Å, 16.6 Å, 16.7 Å, 16.8 Å, 16.9 Å, 17.0 Å, 17.1 Å, 17.2 Å, 17.3 Å, 17.4 Å, 17.5 Å, 17.6 Å, 17.7

Å, 17.8 Å, 17.9 Å, 18.0 Å, 18.1 Å, 18.2 Å, 18.3 Å, 18.4 Å, 18.5 Å, 18.6 Å, 18.7 Å, 18.8 Å., 18.9 Å, 19.0 Å, 19.1 Å, 19.2 Å, 19.3 Å, 19.4 Å, 19.5 Å, 19.6 Å 19.7 Å, 19.8 Å, 19.9 Å and 20.0 Å. An embodiment of the present invention uses a molecular sieve having an average pore size ranging from about 5 Å to about 10 Å to effect the separation. The molecular sieves may optionally be subject to drying by heat and or inert gas purge prior to use as known in the art.

It is understood that in silicalites and zeolites, the pore sizes are substantially uniform, while in carbon molecular sieves the pore sizes are more varied. Thus, the average pore size in the silicalites and zeolites are approximate to the pore sizes therein.

In an embodiment, the molecular sieves having the average pore size described hereinabove and useful for the present invention are carbon molecular sieves. In another embodiment, the molecular sieves having the average pore size described hereinabove and useful for the present invention are Silicalites. In still another embodiment, the molecular sieves having the average pore size described hereinabove and useful for the present invention are zeolites.

The adsorption can occur under static or flow conditions. The temperature, pressure, and contact time for adsorption can vary. In an embodiment, the temperature is in the range of about 0° C. to about 100° C., and in another embodiment, in the range of about 10° C. to about 50° C., and, in another embodiment, in the range of about 20° C. to about 30° C. In another embodiment, the temperature is about room temperature. The pressure can vary and is not critical, e.g. from about 0 psig to 50 psig, in one embodiment, and in another embodiment, of about 0 psig to about 20 psig. In an embodiment, the separation step is effected at ambient pressure, e.g., 1 atm pressure. The contact time, which is defined as the quotient of the adsorbent bed volume divided by the entering volumetric flow rate of the feedstock, may vary but it may affect single pass adsorption percentage of an adsorbate (such as HCFO-1233xf in this case). Operating parameters including temperature, pressure, and contact time are determined by routine experimentation by one of ordinary skill in the art. In one embodiment, after being passed through the solid adsorbent bed, at least 50% of HCFO-1233xf present in HCFC-244bb feed is adsorbed. In another embodiment, after being passed through the solid adsorbent bed, at least 75% of HCFO-1233xf present in HCFC-244bb feed is adsorbed. In another embodiment, after being passed through the solid adsorbent bed, at least 90% of HCFO-1233xf present in HCFC-244bb feed is adsorbed. Yet in another embodiment, after being passed through the solid adsorbent bed, at least 95% of HCFO-1233xf present in HCFC-244bb feed is adsorbed.

As used herein, unless indicated to the contrary, percentage refers to weight percentage.

Unless indicated to the contrary, the term "solid adsorbent" refers to carbon molecular sieves, as described herein and silicalite and zeolites. As described hereinbelow, these solid adsorbents are used to separate 244bb from 1233xf.

As described hereinabove, in the second step of 1234yf synthesis, 1233xf is fluorinated with hydrogen fluoride to make 244bb. This may be effected in the liquid phase or gas phase. The products of the second step from the process described above include HCFC-244bb, unreacted HCFO-1233xf, unreacted HF and small amounts of other halogenated olefins. Upon removal of the HF, a pure organic composition is formed, and it is then available for separation into its component parts by the method of the current invention.

Of particular interest is the existence of a binary azeotrope or azeotrope-like composition of HCFC-244bb and HCFO-1233xf which is formed as disclosed in U.S. Pat. No. 7,803,283, after separating all of the organic impurities from the second step of the process. After a mixture of HCFC-244bb and HCFO-1233xf is separated from impurities, the mixture in a liquid or gaseous form can be contacted with the solid adsorbent of silicalite or carbon molecular sieves, as defined hereinabove that preferentially adsorbs HCFO-1233xf and then essentially pure HCFC-244bb can be recovered HCFO-1233xf that is adsorbed by the solid adsorbent can be recovered by means known in the art such as desorption at elevated temperatures followed by condensation.

In one embodiment, the mixture of HCFC-244bb and HCFO-1233xf is charged into a vessel containing the solid adsorbent maintained at temperature and pressure that are sufficient to keep the mixture liquefied. The 244bb passes through the solid adsorbent, while the 1233xf is adsorbed onto the surface of the solid adsorbent. Then essentially HCFC-244bb is removed from the vessel by filtration. After heating the vessel under vacuum or in the inert gas flow the essentially pure HCFO-1233xf is recovered from the solid adsorbent.

In another embodiment, the liquefied mixture of HCFC-244bb and HCFO-1233xf is continuously fed to a column packed with the solid adsorbent. HCFO-1233xf is adsorbed by the solid adsorbent and essentially pure HCFC-244bb is then collected.

In a third embodiment, the mixture of HCFC-244bb and HCFO-1233xf is continuously fed as a vapor to the column packed with solid adsorbent. HCFO-1233xf is adsorbed on the surface of the solid adsorbent and essentially pure HCFC-244bb collected.

In fourth embodiment, the mixture of HCFC-244bb and HCFO-1233xf is continuously fed as a vapor to the column packed with solid adsorbent. HCFO-1233xf is adsorbed on the surface of the solid adsorbent and essentially pure HCFC-244bb is continuously fed into a vapor phase dehydrochlorination reactor where it is at least partially converted to HFO-1234yf. After separating unreacted HCFC-244bb exiting dehydrochlorination reactor from the HFO-1234yf product and by-products such as HCl and possibly HF, the HCFC-244bb is recycled back into the dehydrochlorination reactor via the purifying column filled with solid adsorbent.

In the embodiments above, the mixture of 244bb and 1233xf are being separated by contacting the solid adsorbent with the mixture under conditions effective to substantially separate 244bb from 1233xf. For example, the separation step is effected for a time sufficient for the 1233xf to be adsorbed on the solid adsorbent. In another embodiment, the separation step is effected for the 244bb to pass through the solid adsorbent, After the loading of an adsorbent, air must be removed using an inert gas (such as nitrogen) purge before introducing 1233xf/244bb stream into the adsorbent vessel. Alternatively, the repetitive pressurization and depressurization of the bed with an inert gas (such as nitrogen) can be used to purge the bed void volume. In an embodiment, the inert gas (such as nitrogen) purge flows down (top to bottom) through the adsorbent vessel to prevent lifting the bed and support material due to high velocities. The purging is continued until the oxygen content of the outlet mixture is at least less than 0.5 volume %. In one embodiment, the adsorption is conducted in the absence of an inert gas (such as nitrogen) as diluent. In another embodiment, the adsorption is conducted in the presence of an inert gas (such as nitrogen or noble gas such as helium, and the like) and the concentration of organic (1233xf/244bb) is slowly increased until a substantially pure organic form is obtained.

After the separation of 244bb and 1233xf, the essentially pure HCFC-244bb can be fed into a dehydrochlorination reactor to produce a product comprising HFO-1234yf.

When the solid adsorbent reaches its saturation of 1233xf, the spent solid adsorbent can be regenerated and be reused using techniques described in U.S. Pat. No. 9,731,271, the contents of which are incorporated by reference.

As used herein, the terms "essentially pure" and "substantially pure" are synonymous. Using the methodology described herein, one can obtain substantially pure HCFC 244bb. By "substantially" pure, it is meant that the HCFC-244bb is at least 99.0% pure. Moreover, it contains less than about 1.0% 1233 xf.

The following non-limiting example further exemplifies the present invention.

Many aspects and embodiments have been described and are merely exemplary and not limiting. After reading the specification, skilled artisans appreciate that other aspects and embodiments are possible without departing from the scope of the invention.

Example 1

A cylindrical Monel reactor of ¾" diameter immersed into a 3-zone electrical furnace was used in all of the experiments of adsorption tests. Process temperatures were recorded using a multi-point thermocouple placed inside the reactor and within the solid adsorbent bed. The distance between two adjacent probe points was 4". The solid adsorbent was loaded in such a way that its bed was within three adjacent probe points. The solid adsorbent was dried in nitrogen flow for 4 hours at 200° C. After drying step, the reactor was cooled down to room temperature (typically between 20° and 30° C.). 244bb feed was then fed into the bottom of the vertically mounted reactor and was vaporized before reaching the bed of solid adsorbent. Effluent gases were periodically analyzed by means of gas chromatograph (GC) to determine the adsorption efficiency of each adsorbent.

Various molecular sieves were tested for adsorbing 1233xf included in 244bb feed with a 244bb feed containing 2.304 GC area % 1233xf. The capacity of each adsorbent was calculated based on individual isothermal adsorption curve and the results are presented in Table 1. The molecular sieve 13X showed the highest adsorption capacity (ca. 1.6 wt % of its own weight). Table 2 presents the performance of 13X. During the effective period of time (where the adsorption percentage of 1233xf was >95%), the 1233xf concentration in effluent stream was below 1000 ppm.

TABLE 1

Capacity of various molecular sieves for adsorbing 1233xf at room temperature atmosphere pressure*

| Adsorbent | Capacity, g-1233xf/ml-adsorbent | Capacity, g-1233xf/g-adsorbent |
|---|---|---|
| 5A | <0.0001 | <0.0001 |
| AW-500 | 0.0003 | 0.0004 |
| MFI(40)-6 (H$^+$ form) | 0.0033 | 0.0046 |
| MFI(300)-6 (H$^+$-silicalite) | 0.0015 | 0.0024 |
| MFI(550)-5 (Na$^+$-silicalite) | 0.0021 | 0.0030 |
| ZSM-5 (SiO$_2$/Al$_2$O$_3$ mole ratio = 50) | 0.0028 | 0.0045 |
| H-ZSM-5 (SiO$_2$/Al$_2$O$_3$ mole ratio = 280) | 0.0012 | 0.0019 |
| 13X | 0.0129 | 0.0159 |

*Feed composition: 97.6957 GC area % 244 bb/2.3043 GC area % 1233xf; 50 ml of adsorbent

TABLE 2

Performance of 13X molecular sieve during 1233xf adsorption at room temperature and atmosphere pressure*

| Period of time, h | Feed passed through, g | Reactor effluent composition, GC area % | | | 1233xf adsorbed, % | 1233xf adsorbed, g |
|---|---|---|---|---|---|---|
| | | 1234yf | 244bb | 1233xf | | |
| 0-1 | 0.6 | 0.0000 | 100.0000 | 0.0000 | 100.0 | 0.0138 |
| 1-2 | 9.6 | 0.0000 | 100.0000 | 0.0000 | 100.0 | 0.2212 |
| 2-3 | 3.7 | 0.0157 | 99.9608 | 0.0235 | 99.0 | 0.0844 |
| 3-4 | 5.7 | 0.0202 | 99.9170 | 0.0628 | 97.3 | 0.1278 |
| 4-5 | 5.5 | 0.0190 | 99.1041 | 0.8769 | 61.9 | 0.0785 |
| 5-6 | 5.4 | 0.0148 | 97.9563 | 2.0288 | 12.0 | 0.0149 |
| 6-7 | 5.6 | 0.0188 | 97.7267 | 2.2545 | 2.2 | 0.0028 |
| 7-8 | 5.2 | 0.0240 | 97.7792 | 2.1968 | 4.7 | 0.0056 |
| 8-9 | 5.4 | 0.0246 | 97.7901 | 2.1853 | 5.2 | 0.0064 |

*Feed composition: 97.6957 GC area % 244bb/2.3043 GC area % 1233xf; 50 ml of adsorbent Example 2

A cylindrical Monel reactor of ¾" diameter immersed into a 3-zone electrical furnace was used in all of the experiments of adsorption tests. Process temperatures were recorded using a multi-point thermocouple placed inside the reactor and within the solid adsorbent bed. The distance between two adjacent probe points was 4". The solid adsorbent was loaded in such a way that its bed was within three adjacent probe points. The solid adsorbent was dried in nitrogen flow for 4 hours at 200° C. After drying step, the reactor was cooled to room temperature. The 244bb feed was then fed into the bottom of the vertically mounted reactor and was vaporized before reaching the bed of solid adsorbent. Effluent gases were periodically analyzed by means of gas chromatograph (GC) to determine the adsorption efficiency of each adsorbent.

Various carbon molecular sieves, such as Shirasagi X2M4/6 obtained from Japan EnviroChemicals, and CMSH255/2 and Shirasagi CT-350 obtained from Carbon-Tech (Germany). were tested for adsorbing 1233xf included in a 244bb feed with a 244bb feed containing 2.3043 GC area % 1233xf. The capacity of each adsorbent was calculated based on individual isothermal adsorption curve and the results are presented in Table 3. The Shirasagi X2M4/6 showed the highest adsorption capacity (ca. 6.2 wt % of its own weight). Table 4 presents the performance of Shirasagi X2M4/6 carbon molecular sieve. During the effective period of time (where the adsorption percentage of 1233xf was >95%), the 1233xf concentration in effluent stream was below 1000 ppm.

TABLE 3

Capacity of various carbon molecular sieves for adsorbing 1233xf at room temperature and atmosphere pressure*

| Adsorbent | Surface area, m²/g | Pore volume, ml/g | Average pore size, Å | Capacity, g-1233xf/ml-adsorbent | Capacity, g-1233xf/g-adsorbent |
|---|---|---|---|---|---|
| Shirasagi X2M4/6 | 508.1 | 0.23 | 17.8 | 0.0318 | 0.0615 |
| CMS H255/2 | 750 | 0.3 | 5 | 0.0286 | 0.0494 |
| Shirasagi CT-350 | 300 | 0.1 | 3 | <0.0001 | <0.0001 |

*Feed composition: 97.6957 GC area % 244 bb/2.3043 GC area % 1233xf; 50 ml of adsorbent

TABLE 4

Performance of Shirasagi X2M4/6 carbon molecular sieve during 1233xf adsorption at room temperature and atmosphere pressure*

| Period of time, h | Feed passed through, g | Reactor effluent composition, GC area % | | | 1233xf adsorbed, % | 1233xf adsorbed, g |
|---|---|---|---|---|---|---|
| | | 1234yf | 244bb | 1233xf | | |
| 0-1 | 4.9 | 0.0000 | 99.9324 | 0.0676 | 96.5348 | 0.1000 |
| 1-2 | 5.1 | 0.0000 | 100.0000 | 0.0000 | 100.0000 | 0.1078 |
| 2-3 | 5.0 | 0.0074 | 99.9926 | 0.0000 | 100.0000 | 0.1057 |
| 3-4 | 5.0 | 0.0000 | 100.0000 | 0.0000 | 100.0000 | 0.1057 |
| 4-5 | 4.9 | 0.0029 | 99.9940 | 0.0032 | 99.8360 | 0.1034 |
| 5-6 | 5.1 | 0.0065 | 99.9816 | 0.0119 | 99.3900 | 0.1071 |
| 6-7 | 5.0 | 0.0133 | 99.9467 | 0.0400 | 97.9496 | 0.1035 |
| 7-8 | 5.1 | 0.0250 | 99.8642 | 0.1108 | 94.3203 | 0.1017 |
| 8-9 | 5.1 | 0.0325 | 99.7882 | 0.1793 | 90.8089 | 0.0979 |
| 9-10 | 5.1 | 0.0369 | 99.5314 | 0.4316 | 77.8757 | 0.0840 |
| 10-11 | 4.9 | 0.0474 | 99.2961 | 0.6566 | 66.3420 | 0.0687 |
| 11-12 | 4.9 | 0.0478 | 98.911 | 1.0412 | 46.6270 | 0.0483 |
| 12-13 | 4.9 | 0.0419 | 98.6312 | 1.3269 | 31.9818 | 0.0331 |
| 13-14 | 5.1 | 0.0381 | 98.511 | 1.4509 | 25.6254 | 0.0276 |
| 14-15 | 4.9 | 0.0336 | 98.363 | 1.6034 | 17.8081 | 0.0184 |
| 15-16 | 5.0 | 0.0301 | 98.2906 | 1.6793 | 13.9174 | 0.0147 |
| 16-17 | 5.0 | 0.0278 | 98.2391 | 1.7331 | 11.1595 | 0.0118 |
| 17-18 | 5.1 | 0.0259 | 98.1925 | 1.7815 | 8.6785 | 0.0094 |
| 18-19 | 5.1 | 0.0244 | 98.1692 | 1.8065 | 7.3970 | 0.0080 |
| 19-20 | 5.1 | 0.0254 | 98.1349 | 1.8397 | 5.6951 | 0.0061 |
| 20-21 | 5.0 | 0.0237 | 98.125 | 1.8512 | 5.1056 | 0.0054 |
| 21-22 | 5.1 | 0.0242 | 98.1068 | 1.8689 | 4.1983 | 0.0045 |
| 22-23 | 5.1 | 0.0231 | 98.0325 | 1.9444 | 0.3281 | 0.0004 |

*Feed composition: 97.6957 GC area % 244bb/2.3043 GC area % 1233xf; 40 ml of adsorbent Many aspects and embodiments have been described and are merely exemplary and not limiting. After reading the specification, skilled artisans appreciate that other aspects and embodiments are possible without departing from the scope of the invention. Other features and benefits of any one or more of the embodiments will be apparent from the hereinabove detailed description and the claims.

What is claimed is:

1. A method for separating 2-chloro-3,3,3-trifluoropropene (HCFO-1233xf) and 2-chloro-1,1,1,2-tetrafluoropropane (HCFC-244bb) comprising contacting a mixture of the HCFO-1233xf and HCFC-244bb with a carbon molecular sieve having an average pore size of 5 Å or greater under conditions effective at a temperature ranging from about 0° to about 100° C. and a pressure ranging from about 0 psig to about 50 psig such that the molecular sieve adsorbs at least a portion of the HCFO-1233xf thereby separating it from the HCFC-244bb and recovering therefrom HCFC-244bb.

2. The method of claim 1 wherein the average pore size is 5.5 Å or greater.

3. The method according to claim 1 where the mixture is passed over the molecular sieve for a period of time sufficient to adsorb HCFO-1233xf.

4. The method according to claim 1 wherein the molecular sieve is added to the mixture for a period of time sufficient to adsorb HCFO-1233xf.

5. The method according to claim 1 where the temperature ranges from about 10° C. to about 50° C.

6. The method according to claim 1 wherein the pressure ranges from about 0 psig to about 20 psig.

7. The method according to claim 1 wherein HCFO-1233xf is additionally recovered.

8. The method according to claim 1 wherein the mixture is passed through the molecular sieve in liquid form or gaseous form.

9. A method for separating 2-chloro-3,3,3-trifluoropropene (HCFO-1233xf) and 2-chloro-1,1,1,2-tetrafluoropropane (HCFC-244bb) comprising contacting a mixture of the HCFO-1233xf and HCFC-244bb with carbon molecular sieve having an average pore size of 5 Å or greater under conditions such that the molecular sieve adsorbs at least a portion of the HCFO-1233xf thereby separating it from the HCFC-244bb and recovering therefrom HCFC-244bb.

10. The method of claim 9 wherein the average pore size is 5.5 Å or greater.

11. The method according to claim 9 where the mixture is passed over the carbon molecular sieve for a period of time sufficient to adsorb HCFO-1233xf.

12. The method according to claim 9 wherein the molecular sieve is added to the mixture for a period of time sufficient to adsorb HCFO-1233xf.

13. The method according to claim 9 conducted at a temperature ranging from about 0° to about 100° C.

14. The method according to claim 9 conducted at a pressure ranging from about 0 to about 50 psig.

15. The method according to claim 1 wherein HCFO-1233xf is additionally recovered.

16. The method according to claim 9 wherein the mixture is passed through the molecular sieve in liquid form or gaseous form.

17. A method of preparing 2,3,3,3-tetrafluoro-1-propene (HFO-1234yf) comprising:
  (a) contacting a first intermediate composition comprising 2-chloro-3,3,3-trifluoropropene (HCFO-1233xf) with HF in the presence of a fluorination catalyst under conditions effective to produce a second intermediate composition comprising 2-chloro-1,1,1,2-tetrafluoropropane (HCFC-244bb) and unreacted HCFO-1233xf;
  (b) separating the unreacted HCFO-1233xf from the HCFC-244bb by contacting the second intermediate composition with a carbon molecular sieve having an average pore size of 5 Å or greater under conditions effective at a temperature ranging from about 0° to about 100° C. such that the molecular sieve adsorbs the unreacted HCFO-1233xf thereby separating it from at least a portion of the HCFC-244bb; and
  (c) dehydrochlorinating at least a portion of the 244bb separated in step (b) to produce a reaction product comprising HFO-1234yf.

18. The method according to claim 17 where in the separating step is conducted at a pressure ranging from about 0 psig to about 50 psig.

19. The method according to claim 18 where the separating step is conducted at a pressure ranging from about 0 psig to about 20 psig.

20. The method according to claim 17 where in the separating step, the mixture is passed over the carbon molecular sieve for a period of time sufficient to adsorb HCFO-1233xf.

21. The method according to claim 17 where in the separating step, the carbon molecular sieve is added to the mixture for a period of time sufficient to adsorb HCFO-1233xf.

22. The method according to claim 17 where the separating step is conducted at a temperature ranging from about 10° C. to about 50° C.

23. The method according to claim 17 wherein HCFO-1233xf is additionally recovered from the separation step.

24. The method according to claim 17 where in the separation step, the mixture is passed through the carbon molecular sieve in liquid form or gaseous form.

25. The method according to claim 17 wherein the average pore size is 5.0 to 17.8 Å.

26. A method of preparing 2,3,3,3-tetrafluoropropene (HFO-1234yf) comprising:
  (a) contacting a first intermediate composition comprising 2-chloro-3,3,3-trifluoropropene (HCFO-1233xf) with HF in the presence of a fluorination catalyst under conditions effective to produce a second intermediate composition comprising 2-chloro-1,1,1,2-tetrafluoropropane (HCFC-244bb) and unreacted HCFO-1233xf;
  (b) separating the unreacted HCFO-1233xf from the HCFC-244bb by contacting the second intermediate composition with carbon molecular sieve having an average pore size of 5 Å or greater under conditions effective such that the molecular sieve adsorbs the unreacted HCFO-1233xf thereby separating it from at least a portion of the HCFC-244bb; and
  (c) dehydrochlorinating at least a portion of the 244bb separated in step (b) to produce a reaction product comprising HFO-1234yf.

* * * * *